(12) United States Patent
Ghosh et al.

(10) Patent No.: US 11,813,462 B2
(45) Date of Patent: *Nov. 14, 2023

(54) SUPPLEMENTATION OF CARDIAC CONDUCTION SYSTEM PACING THERAPY

(71) Applicant: Medtronic, Inc., Minneapolis, MN (US)

(72) Inventors: Subham Ghosh, Blaine, MN (US); Richard Cornelussen, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 359 days.

This patent is subject to a terminal disclaimer.

(21) Appl. No.: 16/815,120

(22) Filed: Mar. 11, 2020

(65) Prior Publication Data

US 2020/0353265 A1 Nov. 12, 2020

Related U.S. Application Data

(60) Provisional application No. 62/844,489, filed on May 7, 2019.

(51) Int. Cl.
*A61N 1/368* (2006.01)
*A61N 1/365* (2006.01)
*A61N 1/39* (2006.01)

(52) U.S. Cl.
CPC ......... *A61N 1/36592* (2013.01); *A61N 1/368* (2013.01); *A61N 1/3956* (2013.01)

(58) Field of Classification Search
CPC .. A61N 1/3627; A61N 1/365; A61N 1/36585; A61N 1/3684; A61N 1/36842; A61N 1/36843

See application file for complete search history.

(56) References Cited

U.S. PATENT DOCUMENTS

| | | | | |
|---|---|---|---|---|
| 3,554,187 A | * | 1/1971 | Glassner | A61B 5/316 600/519 |
| 5,713,946 A | * | 2/1998 | Ben-Haim | A61B 5/06 607/122 |
| 5,938,597 A | * | 8/1999 | Stratbucker | A61N 1/046 600/382 |
| 6,450,172 B1 | * | 9/2002 | Hartlaub | A61N 1/37264 607/32 |
| 7,177,704 B2 | | 2/2007 | Laske et al. | |

(Continued)

OTHER PUBLICATIONS

Sweeney et al., "Analysis of Ventricular Activation Using Surface Electrocardiogramhy to Predict Left Ventricular Reverse Volumetric Remodeling During Cardiac Resynchronization Therapy," Circulation, Feb. 9, 2010, 121(5): 626-34.

(Continued)

*Primary Examiner* — Allen Porter
(74) *Attorney, Agent, or Firm* — Mueting Raasch Group

(57) ABSTRACT

Systems and methods may monitor electrical activity of a patient's heart using electrodes during delivery of cardiac conduction system pacing therapy, generate electrical heterogeneity information (EHI) based on the monitored electrical activity during delivery of cardiac conduction system pacing therapy, and determine whether the cardiac conduction system pacing therapy would benefit from supplemental cardiac pacing therapy based on the generated EHI.

26 Claims, 12 Drawing Sheets

(56) References Cited

U.S. PATENT DOCUMENTS

| | | | |
|---|---|---|---|
| 7,738,954 B1* | 6/2010 | Kroll | A61N 1/36842 607/9 |
| 8,180,428 B2 | 5/2012 | Kaiser et al. | |
| 9,119,959 B2 | 9/2015 | Rys et al. | |
| 9,278,229 B1 | 3/2016 | Reinke et al. | |
| 9,320,446 B2 | 4/2016 | Gillberg et al. | |
| 9,675,579 B2 | 6/2017 | Rock et al. | |
| 2008/0269815 A1* | 10/2008 | Houben | A61N 1/3622 607/9 |
| 2009/0099619 A1 | 4/2009 | Lessmeier et al. | |
| 2012/0283587 A1 | 11/2012 | Gosh et al. | |
| 2012/0284003 A1 | 11/2012 | Gosh et al. | |
| 2013/0116740 A1* | 5/2013 | Bornzin | A61N 1/3756 607/9 |
| 2014/0323882 A1* | 10/2014 | Ghosh | A61N 1/365 600/483 |
| 2016/0030751 A1 | 2/2016 | Ghosh et al. | |
| 2016/0045737 A1 | 2/2016 | Ghosh et al. | |
| 2016/0045738 A1 | 2/2016 | Ghosh et al. | |
| 2016/0045744 A1* | 2/2016 | Gillberg | A61N 1/36842 607/27 |
| 2017/0246460 A1* | 8/2017 | Ghosh | A61B 5/303 |
| 2019/0030332 A1 | 1/2019 | Ghosh et al. | |
| 2019/0111270 A1 | 4/2019 | Zhou | |
| 2019/0290909 A1 | 9/2019 | Ghosh et al. | |

OTHER PUBLICATIONS

Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.

Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.

(PCT/US2020/023538) Written Opinion of the International Searching Authority and International Search Report, dated Jun. 29, 2020, 10 pages.

* cited by examiner

SUPPLEMENTATION OF CARDIAC CONDUCTION SYSTEM PACING THERAPY

The disclosure herein relates to systems and methods for use in determining whether cardiac conduction system pacing therapy would benefit from supplemental cardiac pacing therapy and in adjusting such supplemental cardiac pacing therapy.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

SUMMARY

The illustrative systems and methods described herein may be configured to assist a user (e.g., a physician) determining whether cardiac conduction system pacing therapy may benefit from supplemental cardiac pacing therapy and to adjust any supplemental cardiac pacing therapy used in conjunction with cardiac conduction system pacing therapy. Further, the illustrative systems and methods described herein may be configured to assist a user (e.g., a physician) determining whether the patient has a left ventricular or right ventricular delay due to, e.g., a bundle branch block and degrees of correction of the delay through the conduction pacing systems.

In one or more embodiments, the systems and methods may be described as being noninvasive. For example, in some embodiments, the systems and methods may not need, or include, implantable devices such as leads, probes, sensors, catheters, implantable electrodes, etc. to monitor, or acquire, a plurality of cardiac signals from tissue of the patient for use in determining the degree of correction of activation delays in certain regions of the heart (e.g., left side of the heart) by conduction system pacing and whether cardiac conduction system pacing therapy may benefit from supplemental cardiac pacing therapy and to adjust any supplemental cardiac pacing therapy used in conjunction with cardiac conduction system pacing therapy. Instead, the systems and methods may use electrical measurements taken noninvasively using, e.g., a plurality of external electrodes attached to the skin of a patient about the patient's torso. In one or more embodiments, the systems and methods may be described as being invasive in that such systems and methods may utilize implantable electrodes to monitor electrical activity for using in determining, or evaluating, cardiac conduction system capture and/or A-V block. Additionally, it is be understood that both invasive and non-invasive apparatus and processes may be used at the same time or simultaneously in some embodiments.

It may be described that the present disclosure includes selection of cardiac conduction system pacing and traditional left ventricular pacing therapy based on ECG belt surface mapping of activation. Cardiac conduction system pacing in the form of one or more of ventricle-from-atrium (VfA), intraseptal left ventricular (LV) endocardial pacing, and His bundle pacing may benefit some heart failure patients who have electrical delay in the left heart (e.g., due to left bundle branch block) by correcting the left heart delay or in the right heart (e.g., due to right bundle branch block) by correcting the right heart delay. However, other patients may exist where left or right heart delay may not be fully corrected through such cardiac conduction system pacing, and an additional left or right ventricular pacing lead or leadless pacing device may be used to mitigate the remaining delays in electrical activation in the left or right ventricle. The supplemental cardiac pacing may also target other parts of the conduction system, for example, His bundle or right bundle in case of VfA or intraseptal left ventricular endocardial pacing being the primary conduction system pacing target.

The illustrative systems may execute and the illustrative methods may include mapping surface activation and using metrics and ranges of metrics and such surface activation maps to provide quantitative and qualitative feedback on correction of left or right ventricular delay with conduction system pacing (such as VfA), intraseptal pacing by penetrating a lead or a leadless device through the interventricular septum, or His bundle or bundle branch pacing with a traditional lead. The illustrative systems and methods may be used during implantation to gain feedback on the degree of correction of left or right ventricular activation delay. Accordingly, in one example, an implanter may choose to implant an additional lead for left ventricular pacing using the illustrative systems and methods. Further, the illustrative systems and methods may also be employed for decisions to implant a right ventricular lead for correction of right ventricular activation delay.

In one or more embodiments, ECG belt heterogeneity, or dyssynchrony, metrics such as standard deviation of surrogate electrical activation times (SDAT) and average of surrogate electrical activation times (LVAT) from external electrodes positioned on the left side of the patient's thorax may be used to assess the degree of correction of left ventricular activation delay during delivery of pacing therapy (e.g., VfA pacing, intra-septal LV endocardial pacing, His bundle pacing, left bundle branch pacing, etc.) with leaded or leadless devices. The degree of overall resynchronization may be assessed using, e.g., changes in SDAT and LVAT, and one or more pacing settings such as, e.g., position, site of pacing, angle, pacing parameters (timing, outputs, vectors, etc.) may be adjusted to, e.g., optimize the cardiac conduction system pacing therapy.

In one or more embodiments, first, it may be determined whether a basic minimum reduction in dyssynchrony has occurred in response to optimized cardiac conduction system pacing. In one example, a basic minimum reduction in dyssynchrony may be indicated by at least a 10% reduction in SDAT or a 30% reduction in LVAT without SDAT worsening by more than 10%. Then, a metric of assessing the degree of correction or normalization of activation in the left ventricle may be evaluated based on the value of LVAT during such optimized cardiac conduction system pacing.

The illustrative systems and methods may be described as determining the degree of correction of left heart delay. Complete correction of left heart delay may be indicated by an LVAT that is less than or equal to about 30 milliseconds (ms). Intermediate correction of left heart delay (e.g., a slight delay in left ventricular activation) may be indicated by an LVAT between about 30 ms and 50 ms. No correction of left heart delay (e.g., persistent delay in left ventricular activation) may be indicated by an LVAT that is greater than or equal to about 50 ms.

The illustrative systems and methods may indicate that an additional left ventricular pacing lead (for example, in the coronary sinus/lateral wall) may be useful for patients who have persistent delay where conduction system pacing is not able to correct the left heart delay (e.g., bundle branch block). Further, the illustrative systems and methods may indicate that an additional left ventricular pacing lead may be useful for patient who in cases where the basic minimum reductions in dyssynchrony were not achieved.

The illustrative systems and methods may also be used when determining whether to implant a right ventricular lead in patients where the area of delay is in the right ventricle in a similar manner as described herein with respect to the left ventricle but instead utilizing right side oriented electrical heterogeneity metrics or values.

The illustrative systems and methods may be described as assessing the degree of correction of left or right ventricular activation delay and determining whether an additional lead implantation for patients who are not completely corrected may lead to a further augmented therapy combining cardiac conduction system pacing with traditional ventricular pacing.

One illustrative system may include electrode apparatus comprising a plurality of electrodes to monitor electrical activity from tissue of a patient and computing apparatus comprising processing circuitry and coupled to the electrode apparatus. The computing apparatus may be configured to monitor electrical activity of the patient's heart using one or more electrodes of the plurality of electrodes during delivery of cardiac conduction system pacing therapy, generate electrical heterogeneity information (EHI) based on the monitored electrical activity during delivery of cardiac conduction system pacing therapy, and determine whether the cardiac conduction system pacing therapy would benefit from supplemental cardiac pacing therapy based on the generated EHI.

One illustrative method may include monitoring electrical activity of the patient's heart using one or more electrodes of a plurality of electrodes during delivery of cardiac conduction system pacing therapy, generating electrical heterogeneity information (EHI) based on the monitored electrical activity during delivery of cardiac conduction system pacing therapy, and determining whether the cardiac conduction system pacing therapy would benefit from supplemental cardiac pacing therapy based on the generated EHI.

One illustrative system may include electrode apparatus comprising a plurality of electrodes to monitor electrical activity from tissue of a patient and computing apparatus comprising processing circuitry and coupled to the electrode apparatus. The computing apparatus mayb e configured to monitor electrical activity of the patient's heart using one or more electrodes of the plurality of electrodes during delivery of cardiac conduction system pacing therapy and supplemental cardiac pacing therapy, generate electrical heterogeneity information (EHI) based on the monitored electrical activity during delivery of cardiac conduction system pacing therapy and supplemental cardiac pacing therapy, and adjust one or more pacing settings of one or both of cardiac conduction system pacing therapy and supplemental cardiac pacing therapy based on the generated EHI.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF ILLUSTRATIVE EMBODIMENTS

Figure 1:
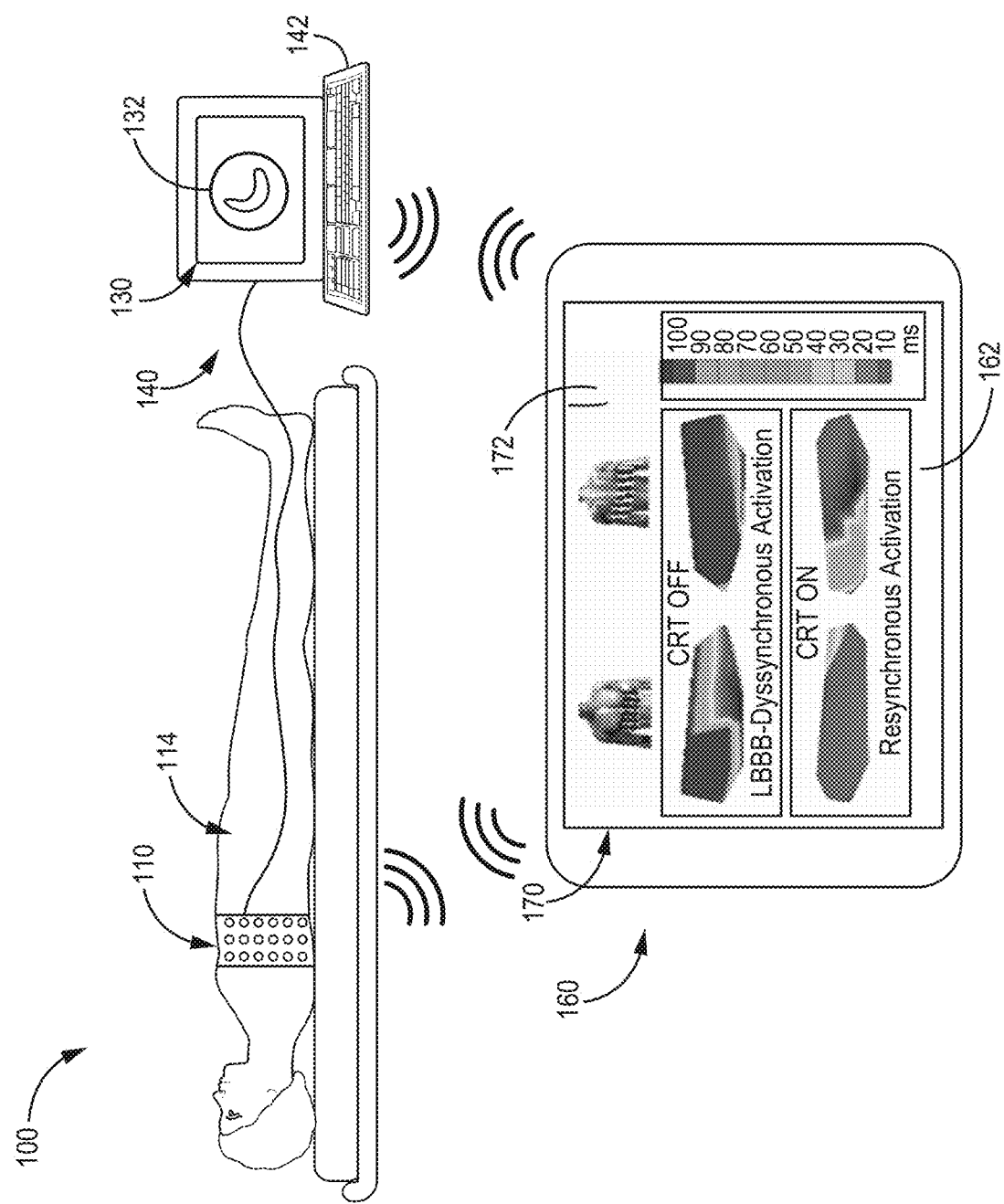
FIG. 1 is a diagram of an illustrative system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative systems and methods shall be described with reference to FIGS. 1-10. It will be apparent to one skilled in the art that elements or processes from one embodiment may be used in combination with elements or processes of the other embodiments, and that the possible embodiments of such systems, methods, and devices using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Various illustrative systems, methods, and graphical user interfaces may be configured to use electrode apparatus including external electrodes, display apparatus, and computing apparatus to noninvasively assist a user (e.g., a physician) in the evaluation of cardiac conduction system pacing therapy and supplemental cardiac pacing therapy and/or the configuration (e.g., optimization) thereof. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 114. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

The computing apparatus 140 and the remote computing device 160 may each include display apparatus 130, 170, respectively, that may be configured to display data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the assessment and evaluation of cardiac conduction system pacing therapy and/or supplemental cardiac pacing therapy. More specifically, for example, the QRS complex of a single cardiac cycle may be evaluated for one or more metrics such as, e.g., QRS onset, QRS offset, QRS peak, various electrical heterogeneity information (EHI) such as electrical activation times, left ventricular or thoracic standard deviation of electrical activation times (LVED), standard deviation of activation times (SDAT), average left ventricular or thoracic surrogate electrical activation times (LVAT), and referenced to earliest activation time, QRS duration (e.g., interval between QRS onset to QRS offset), difference between average left surrogate and average right surrogate activation times, relative or absolute QRS morphology, differences between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, or a tablet computer. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining EHI, for determining QRS onsets, QRS offsets, medians, modes, averages, peaks or maximum values, valleys or minimum values, for determining electrical activation times, for determining whether cardiac conduction system pacing therapy would benefit from supplemental cardiac pacing therapy, for determining whether the patient has left or right ventricular delays or blocks, for determining whether one or more adjustments to pacing settings of cardiac conduction system pacing therapy and supplemental cardiac pacing therapy are beneficial, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of cardiac conduction system pacing therapy configuration information, supplemental cardiac pacing therapy configuration information, left or right ventricular delay or block information, and electrical heterogeneity information.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

It is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for executing, or performing, the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or nonvolatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
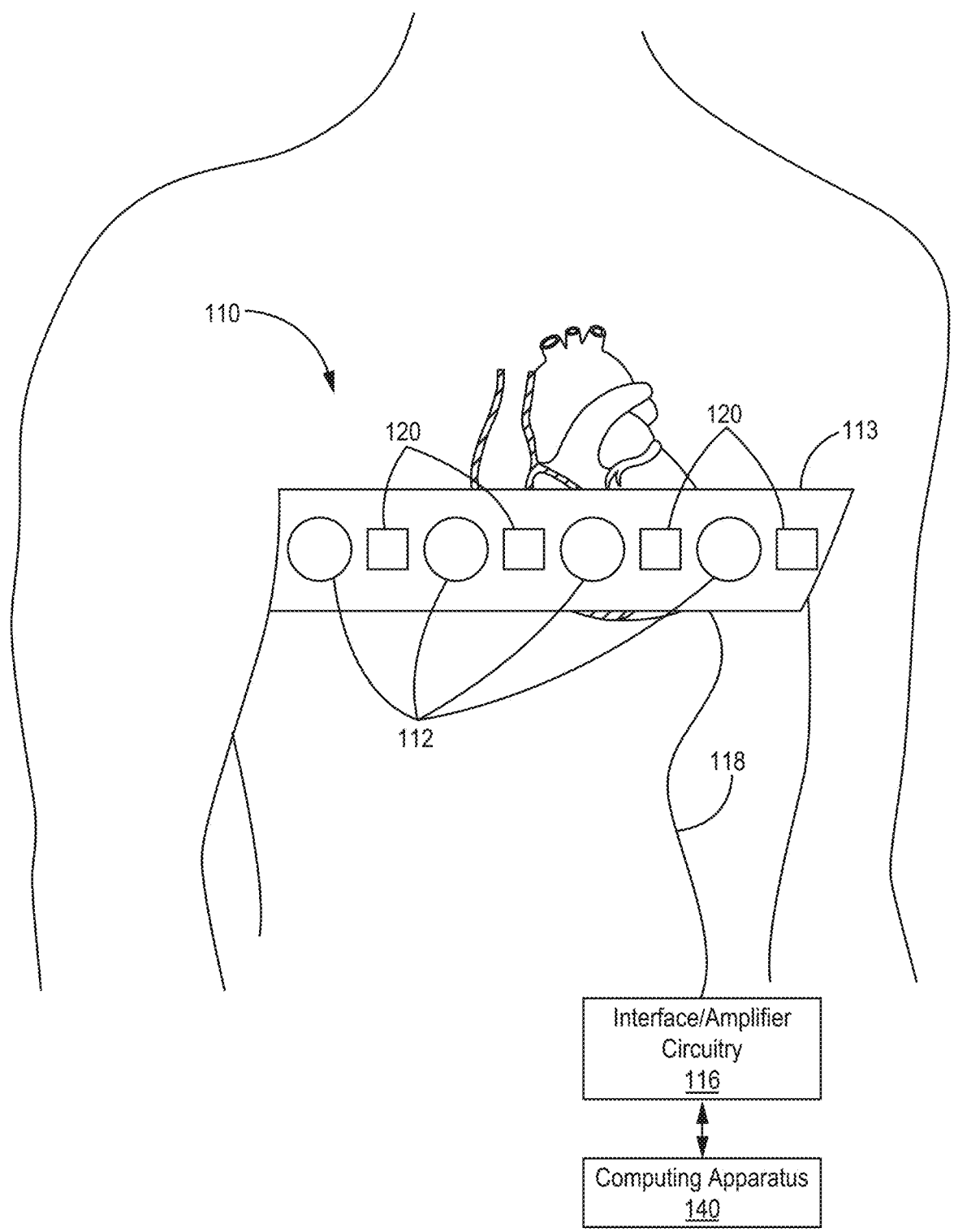
FIGS. 2-3 are diagrams of illustrative external electrode apparatus for measuring torso-surface potentials.

The illustrative electrode apparatus 110 may be configured to measure body-surface potentials of a patient 114 and, more particularly, torso-surface potentials of a patient 114. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 114 such that the electrodes 112 surround the patient's heart. As further illustrated, the electrodes 112 may be positioned around the circumference of a patient 114, including the posterior, lateral, posterolateral, anterolateral, and anterior locations of the torso of a patient 114.

The illustrative electrode apparatus 110 may be further configured to measure, or monitor, sounds from the patient 114 (e.g., heart sounds from the torso of the patient). As shown in FIG. 2, the illustrative electrode apparatus 110 may include a set, or array, of acoustic sensors 120 attached, or coupled, to the strap 113. The strap 113 may be configured to be wrapped around the torso of a patient 114 such that the acoustic sensors 120 surround the patient's heart. As further illustrated, the acoustic sensors 120 may be positioned around the circumference of a patient 114, including the posterior, lateral, posterolateral, anterolateral, and anterior locations of the torso of a patient 114. Further, it is be understood that the illustrative electrode apparatus 110 may include additional sensor apparatus beyond electrode and acoustic sensors such as, for example, a plurality of accelerometers arranged in an array configured to capture motion of the torso of the patient. Still further, each such sensing modality (e.g., electrical, acoustic, motion, etc.) may be used by themselves or in conjunction with one another to provide one or more metrics of heterogeneity or dyssynchrony.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to one or both of the computing apparatus 140 and the remote computing device 160 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 114. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 114. Still further, in other examples, one or both of the electrodes 112 and the acoustic sensors 120 may be part of, or located within, two sections of material or two patches. One of the two patches may be located on the anterior side of the torso of the patient 114 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 114 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 114 across the left side of the patient 114 to the posterior side of the patient 114. Yet still further, in other examples, one or both of the electrodes 112 and the acoustic sensors 120 may be arranged in a curve around the armpit area and may have an electrode/sensor-density that is less dense on the right thorax that the other remaining areas.

The electrodes 112 may be configured to surround the heart of the patient 114 and record, or monitor, the electrical signals associated with the depolarization and repolarization of the heart after the signals have propagated through the torso of a patient 114. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 114. Instead, the electrodes 112 and acoustic sensors 120 may be arranged in an array that extends only part of the way or partially around the patient 114. For example, the electrodes 112 and acoustic sensors 120 may be distributed on the anterior, posterior, and left sides of the patient with less or no electrodes and acoustic sensors proximate the right side (including posterior and anterior regions of the right side of the patient).

One or both of the computing apparatus 140 and the remote computing device 160 may record and analyze the torso-surface potential signals sensed by electrodes 112 and the sound signals sensed by the acoustic sensors 120, which are amplified/conditioned by the interface/amplifier circuitry 116. Further, one or both of the computing apparatus 140 and the remote computing device 160 may be configured to analyze the electrical signals from the electrodes 112 to provide electrocardiogram (ECG) signals, information such as EHI, or data from the patient's heart as will be further described herein. Still further, one or both of the computing apparatus 140 and the remote computing device 160 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict electrical activation maps and EHI obtained using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient. More specifically, the illustrative systems and methods may noninvasively use the electrical information collected using the electrode apparatus 110 to determine whether the patient may benefit from supplemental cardiac pacing therapy to be used in conjunction with already-delivered cardiac conduction system pacing therapy.

Further, the electrode apparatus 110 may further include reference electrodes and/or drive electrodes to be, e.g. positioned about the lower torso of the patient 114, that may be further used by the system 100. For example, the electrode apparatus 110 may include three reference electrodes, and the signals from the three reference electrodes may be combined to provide a reference signal. Further, the electrode apparatus 110 may use three caudal reference electrodes (e.g., instead of standard reference electrodes used in a Wilson Central Terminal) to get a "true" unipolar signal with less noise from averaging three caudally located reference signals.

Figure 3:
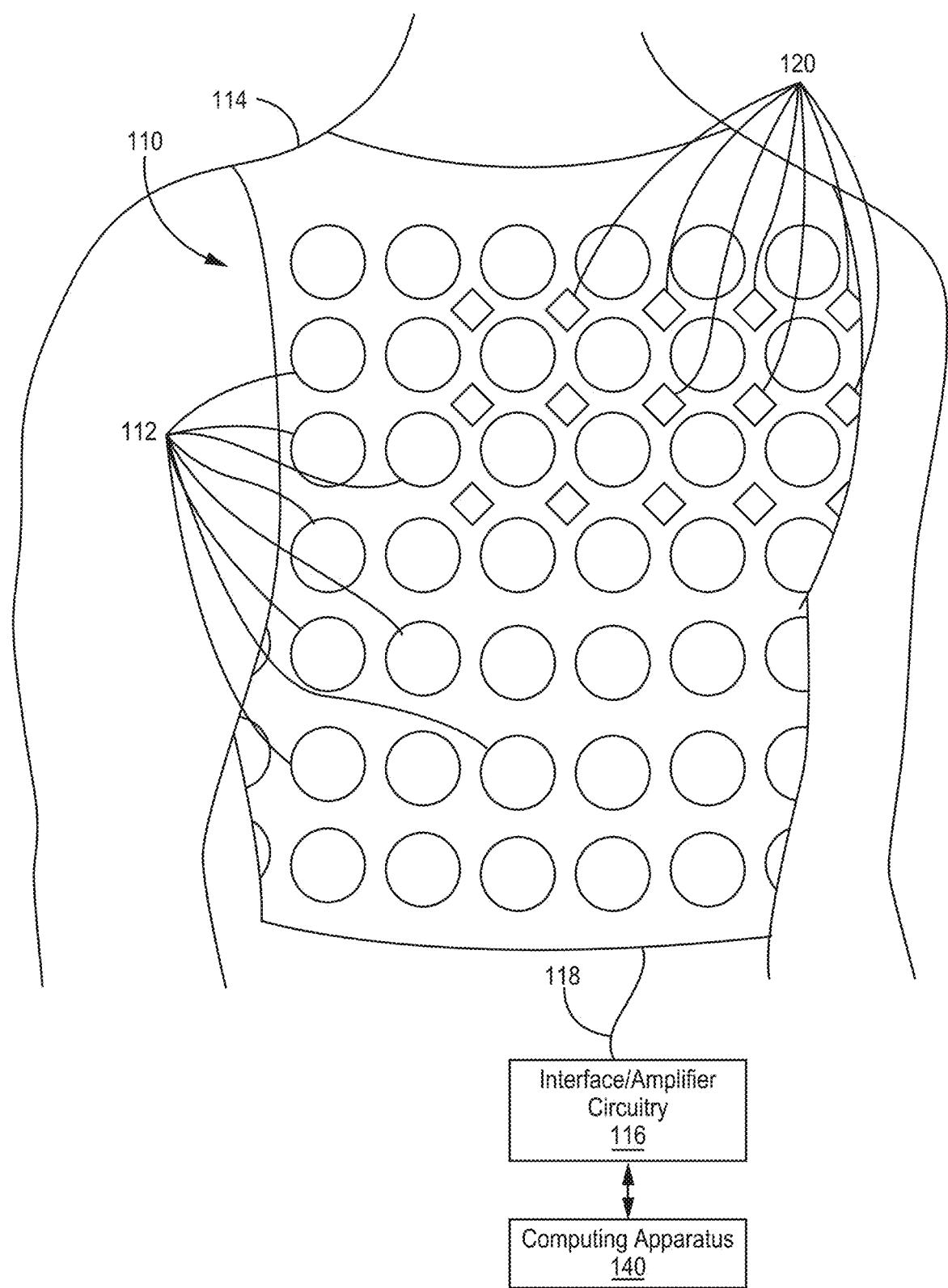

FIG. 3 illustrates another illustrative electrode apparatus 110 that includes a plurality of electrodes 112 configured to surround the heart of the patient 114 and record, or monitor, the electrical signals associated with the depolarization and repolarization of the heart after the signals have propagated through the torso of the patient 114 and a plurality of acoustic sensors 120 configured to surround the heart of the patient 114 and record, or monitor, the sound signals associated with the heart after the signals have propagated through the torso of the patient 114. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 114, including, for example, the posterior, lateral, posterolateral, anterolateral, and anterior locations of the torso of a patient 114.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 114. Further, the vest 114 may be marked to assist in determining the location of the electrodes 112 and the acoustic sensors 120 on the surface of the torso of the patient 114. In some examples, there may be about 25 to about 256 electrodes 112 and about 25 to about 256 acoustic sensors 120 distributed around the torso of the patient 114, though other configurations may have more or fewer electrodes 112 and more or fewer acoustic sensors 120.

The illustrative systems and methods described herein may be used to provide noninvasive assistance to a user in the evaluation of a patient's cardiac health and/or evaluation and configuration of cardiac therapy being presently-delivered to the patient (e.g., by an implantable medical device delivering cardiac conduction system pacing such as a VfA pacing device, by an implantable medical device delivering conventional pacing therapy such as left ventricular pacing therapy using as a left ventricular (LV) coronary sinus lead, etc.). For example, the illustrative systems and methods may be used to assist a user in determining whether cardiac conduction system pacing therapy may benefit from supplemental cardiac pacing therapy and in adjusting one or both of the cardiac conduction system pacing therapy and supplemental cardiac pacing therapy. Further, for example, the illustrative systems and methods may be used to assist a user in the correction of left or right ventricular delays due to, e.g., left or right bundle branches blocks, through the use and configuration of cardiac conduction system pacing therapy and supplemental cardiac pacing therapy.

Figure 4:
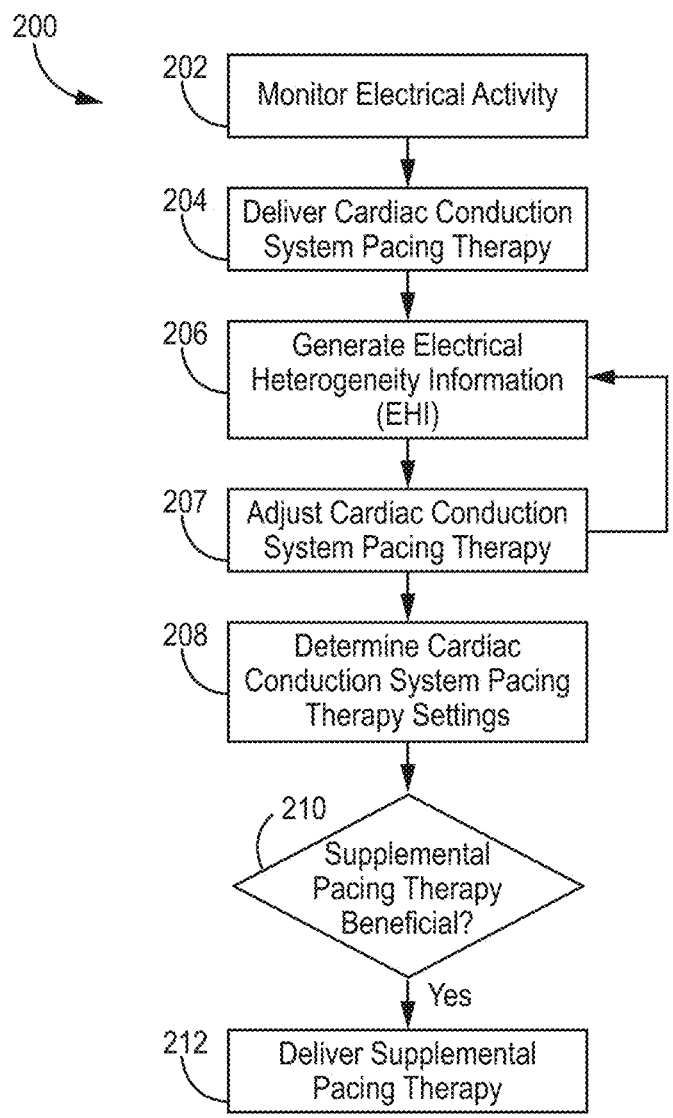
FIG. 4 is a block diagram of an illustrative method of determining whether the cardiac conduction system pacing therapy would benefit from supplemental cardiac pacing therapy.

An illustrative method 200 of determining whether cardiac conduction system pacing therapy would benefit from supplemental cardiac pacing therapy is depicted in FIG. 4. Generally, it may be described that the illustrative method 200 may be used to analyze external electrical activity (e.g., from the torso of the patient) during delivering of cardiac conduction system pacing therapy and use such electrical activity to determine whether such cardiac conduction system pacing therapy may benefit from supplemental cardiac pacing therapy. The supplemental cardiac pacing therapy may be referred to as "supplemental" cardiac pacing therapy because it would be used in conjunction with the cardiac conduction system pacing therapy. For example, the cardiac conduction system pacing therapy may deliver pacing to the cardiac conduction system and the supplemental cardiac pacing may deliver pacing to different areas of the cardiac conduction (i.e., different than the areas which the original cardiac conduction system pacing is delivered) and to areas of the heart other than the cardiac conduction system such a muscular heart tissue (e.g., via conventional pacing therapies).

As shown, the method 200 may include monitoring electrical activity 202. In one embodiment, the electrical activity may be measured externally from the patient. In other words, the electrical activity may be measured from tissue outside the patient's body (e.g., skin). For example, the method 200 may include monitoring, or measuring, electrical activity using a plurality of external electrodes such as, e.g., shown and described with respect to FIGS. 1-3. In one embodiment, the plurality of external electrodes may be part, or incorporated into, a vest or band that is located about a patient's torso. More specifically, the plurality of electrodes may be described as being surface electrodes positioned in an array configured to be located proximate the skin of the torso of a patient. It may be described that when using a plurality of external electrodes, the monitoring process 202 may provide a plurality electrocardiograms (ECGs), signals representative of the depolarization and repolarization of the patient's heart, and/or a plurality of activation times. More specifically, the plurality of ECGs may, in turn, be used to generate activation times representative of the depolarization of the heart.

Cardiac conduction system pacing therapy, as opposed to pacing therapy delivered to other cardiac tissue, delivers electrical pacing pulses to engage in whole or in part the cardiac conduction system that may result in a fast propagation of electrical activation providing a low degree of electrical heterogeneity of activation across the ventricles. The cardiac conduction system includes a specialized network of cells comprising the left and right bundle branches as well as a highly-branched network of specialized Purkinje fibers that aids in rapid propagation of electrical activation across the ventricles, which may lead to a very synchronized activation of the heart. The cardiac conduction system is part of the natural pathway of electrical conduction that extends to the ventricles via the A-V node.

In contrast, in conventional pacing therapy, electrical pacing pulses are delivered to tissue other than the cardiac conduction system such that electrical activation propagates from one myocardial cell to another myocardial cell (also referred to as "cell-to-cell"), which may be slower and asynchronous without any involvement of the specialized cardiac conduction system. In at least one embodiment, it may be described that conventional pacing therapy delivers pacing pulses to muscular heart tissue so as to depolarize the muscular heart tissue.

The method 200 may include delivery of cardiac conduction system pacing therapy 204. The cardiac conduction system pacing therapy may utilize any implantable or non-implantable cardiac pacing system intended to pace or deliver electrical paces to one or more areas or regions of the cardiac conduction system of the patient. The cardiac conduction system pacing therapy may use a single pacing electrode defining a single pacing vector or a plurality of pacing electrodes defining a plurality of pacing vectors.

One example of cardiac conduction system pacing therapy may be ventricle from atrium (VfA) pacing therapy described and shown herein with respect to FIGS. 7-10. The VfA pacing therapy may be configured to deliver electrical paces to one or more areas of the cardiac conduction system including, but not limited to areas of the left bundle branches and the right bundle branches.

Another example of cardiac conduction system pacing therapy may be His bundle pacing therapy as, e.g., described in U.S. patent application Ser. No. 16/163,132 filed Oct. 17, 2018, entitled "His Bundle and Bundle Branch Pacing Adjustment," which is incorporated herein by reference in its entirety. Still another example of cardiac conduction system pacing therapy may be intraseptal left ventricular endocardial pacing therapy as, e.g., described in U.S. Pat. No. 7,177,704 issued on Feb. 13, 2007, entitled "Pacing Method and Apparatus," which is incorporated herein by reference in its entirety.

During the delivery of the cardiac conduction system pacing therapy 204, the electrical activity may continue to be monitored 202, and may be used to generate electrical heterogeneity information (EHI) 206. The EHI (e.g., data) may be defined as information indicative of at least one of mechanical synchrony or dyssynchrony of the heart and/or electrical synchrony or dyssynchrony of the heart. In other words, EHI may represent a surrogate of actual mechanical and/or electrical functionality of a patient's heart. In at least one embodiment, relative changes in EHI (e.g., from baseline heterogeneity information to therapy heterogeneity information, from a first set of heterogeneity information to a second set of therapy heterogeneity information, etc.) may be used to determine a surrogate value representative of the changes in hemodynamic response (e.g., acute changes in LV pressure gradients). Left ventricular pressure may be typically monitored invasively with a pressure sensor located in the left ventricular of a patient's heart. As such, the use of EHI to determine a surrogate value representative of the left ventricular pressure may avoid invasive monitoring using a left ventricular pressure sensor.

In at least one embodiment, the EHI may include a standard deviation of ventricular activation times measured using some or all of the external electrodes, e.g., of the electrode apparatus 110 described herein with respect FIGS. 1-3. Further, local, or regional, EHI may include standard deviations and/or averages of activation times measured using electrodes located in certain anatomic areas of the torso. For example, external electrodes on the left side of the torso of a patient may be used to compute local, or regional, left EHI.

The EHI may be generated using one or more various systems and/or methods. For example, EHI may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

EHI may include one or more metrics or indices. For example, one of the metrics, or indices, of electrical heterogeneity may be a standard deviation of activation times (SDAT) measured using some or all of the electrodes on the surface of the torso of a patient. In some examples, the SDAT may be calculated using the estimated cardiac activation times over the surface of a model heart.

Another metric, or index, of electrical heterogeneity, or dyssynchrony, may be a left standard deviation of surrogate electrical activation times (LVED) monitored by external electrodes located proximate the left side of a patient. Further, another metric, or index, of electrical heterogeneity may include an average of surrogate electrical activation times (LVAT) monitored by external electrodes located proximate the left side of a patient. The LVED and LVAT may be determined (e.g., calculated, computed, etc.) from electrical activity measured only by electrodes proximate the left side of the patient, which may be referred to as "left" electrodes. The left electrodes may be defined as any surface electrodes located proximate the left ventricle, which includes the body or torso regions to the left of the patient's sternum and spine (e.g., toward the left arm of the patient, the left side of the patient, etc.). In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left and right sides of the heart as determined using imaging apparatus (e.g., x-ray, fluoroscopy, etc.).

Another illustrative metric, or index, of electrical heterogeneity, or dyssynchrony, right ventricular activation time (RVAT) of electrodes on the right side of the torso of the patient. A metric of RVAT may be determined from right electrodes on both the anterior and posterior surfaces. The right electrodes may be defined as any surface electrodes located proximate the right ventricle, which includes the body or torso regions to the right of the patient's sternum and spine (e.g., toward the right arm of the patient, the right side of the patient, etc.). Further, the RVAT may be mean, median, or another statistical composite value based on, or computed from, the electrical signals from a right set of electrodes on the right side of the torso of the patient (e.g., right torso of the patient).

Another illustrative metric, or index, of electrical heterogeneity, or dyssynchrony, may be a range of activation times (RAT) that may be computed as the difference between the maximum and the minimum torso-surface or cardiac activation times, e.g., overall or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

Another illustrative metric, or index, of electrical heterogeneity, or dyssynchrony, may include estimates of a percentage of surface electrodes located within a particular region of interest for the torso or heart whose associated activation times are greater than a certain percentile, such as, for example the 70th percentile, of measured QRS complex duration or the determined activation times for surface electrodes. The region of interest may, e.g., be a posterior, left anterior, and/or left-ventricular region. The illustrative metric, or index, may be referred to as a percentage of late activation (PLAT). The PLAT may be described as providing an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, the EHI may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Heterogeneity information may also include measurements of improved cardiac mechanical function measured by imaging or other systems to track motion of implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZAING CRT THERAPY" and published on Apr. 16, 2009, each of which is incorporated herein by reference in its entirety.

The illustrative method 200 may further including adjusting, or modifying, the cardiac conduction system pacing therapy 207 to, for example, optimize the cardiac conduction system pacing therapy to provide effective heart functionality. The method 200 may adjust the cardiac conduction system pacing therapy 207 in various ways. For example, the cardiac conduction system pacing therapy may include, or define, a plurality of different pacing settings, or parameters, that may be adjusted. The plurality of pacing settings may include, but not be limited to, pacing electrode location, pacing electrode angle, pacing amplitude or power, pacing times such as A-V delay, V-V delay, and pacing pulse length, use of one or more pacing electrodes, and use of one or more pacing vectors. In other words, one or more of the pacing settings may be changed (e.g., increase, decreased, moved, etc.) during adjustment of the cardiac conduction system pacing therapy 207.

After adjusting the cardiac conduction system pacing therapy 207, the method 200 may return to generating EHI 206 from the electrical activity monitored during the newly-adjusted cardiac conduction system pacing therapy. Then, the method 200 may again adjust the cardiac conduction system pacing therapy 207, generate EHI 206, and continue looping until a plurality of different cardiac conduction system pacing therapy configurations, each having at least one different pacing parameter, have been attempted. In one embodiment, the pacing settings may be adjusted incrementally by steps or percentages in a way that "sweeps" across a range of possible parameters for each particular setting. For example, A-V delay may start at a level equal to 70% of patient's intrinsic A-V delay and may be progressively decreased in steps of about 10 ms to about 20 ms until a predefined minimum of 60 ms. Additionally, for example, the paced setting may be location or angle of the pacing electrode, and the location or angle of the pacing electrode may be adjusted incrementally by an implanter to provide a range of different locations and angles.

It may be described that processes 206, 207 define a "closed-loop." For example, processes 206, 207 may continue looping for a plurality of different pacing settings or configurations, and for each of the plurality of different pacing settings or configurations, EHI information may be generated 206. The EHI generated for the plurality of different pacing settings or configurations may then be used to determine selected pacing settings of the cardiac conduction system pacing therapy 208. The selected pacing settings for the cardiac conduction system pacing therapy may, in some embodiments, be referred to as the "optimal" pacing settings as, for example, the pacing settings providing the most effective cardiac functionality may be selected. It is to be understood, however, the pacing settings providing the most effective cardiac functionality may not necessarily be the pacing settings that would be selected as considerations other than cardiac functionality exist such as, for example, battery life of the device performing the therapy. Thus, the selected, or optimal, pacing settings for the cardiac conduction system pacing therapy may represented a balance of many factors including cardiac functionality.

For example, SDAT may be utilized to determine the selected pacing settings for the cardiac conduction system pacing therapy 208. As such, a plurality of different pacing settings may be utilized 207, and an SDAT may be generated for each of the plurality of different pacing settings 206. In this example, the lowest SDAT may be indicative of the most effective pacing settings for the cardiac conduction system pacing therapy, and thus, the cardiac conduction system pacing therapy settings having, or corresponding to, the lowest SDAT may be selected 208 to be used with the cardiac conduction system pacing therapy.

Various thresholds may be utilized to determine whether paced settings are acceptable for selection or use. For instance, a selected percentage reduction in an EHI metric from baseline taken prior to therapy may be utilized. In one embodiment, the pacing settings of the cardiac conduction system pacing therapy resulting in a basic minimum reduction in the EHI may be selected as the selected (e.g., optimal) pacing settings. For example, pacing settings resulting in a 10% reduction from baseline SDAT (e.g., baseline SDAT may be determined prior to the delivery of cardiac conduction system pacing therapy) may be selected. Further, for example, pacing settings resulting in a 30% reduction from baseline LVAT (e.g., baseline LVAT may be determined prior to the delivery of cardiac conduction system pacing therapy) without SDAT worsening by 10% or more from baseline SDAT may be selected.

Further illustrative systems, methods, and processes for optimizing the cardiac conduction system pacing therapy may be described in U.S. patent application Ser. No. 15/934, 517 filed on Mar. 23, 2019 entitled "Evaluation of Ventricle from Atrium Pacing Therapy" and U.S. Prov. Pat. App. Ser. No. 62/725,763 filed on Aug. 31, 2018 entitled "Adaptive VFA Cardiac Therapy," each of which is incorporated herein by reference in its entirety.

The selected pacing settings for the cardiac conduction system pacing therapy may, however, still result in a left or right ventricular delay, for example, due to a left or right ventricular bundle branch block. Thus, even though a global metric of electrical heterogeneity such as SDAT may indicate effective cardiac conduction system therapy, a left or right ventricular delay may exist, which may be corrected through supplemental cardiac pacing therapy. The supplemental cardiac pacing therapy may deliver pacing to areas of the cardiac conduction system that are different from the cardiac conduction system pacing therapy already being delivered and/or to areas of the heart other than the cardiac conduction system such as, e.g., muscular heart tissue.

Figure 5A:
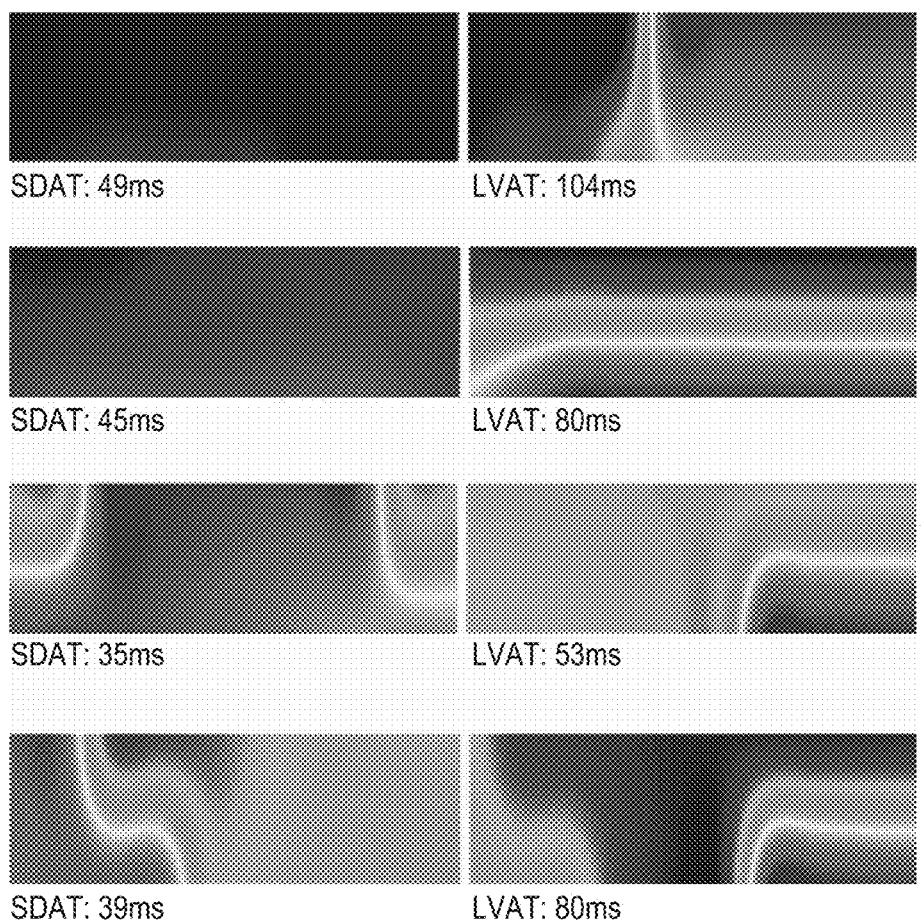
FIG. 5A depicts illustrative anterior and posterior electrical activation maps depicting no cardiac resynchronization with poor to partial posterior preactivation during left ventricular basal septal pacing.

For example, four sets of surrogate electrical activation maps are depicted FIG. 5A that have no cardiac resynchronization with poor to partial posterior preactivation during left ventricular basal septal pacing. Each set includes an anterior activation map on the left, a posterior activation map on the right, and EHI, namely SDAT and LVAT, depicted below each map. As shown, each of the sets has a relatively-low SDAT (e.g., less than 50 ms), which may have been provided using a "closed loop" method similar to as described herein with respect to processes 206, 207, 208. However, each of the sets also has a high LVAT (e.g., three sets greater than 75 ms) indicating no cardiac resynchronization with poor to partial posterior preactivation.

Figure 5B:
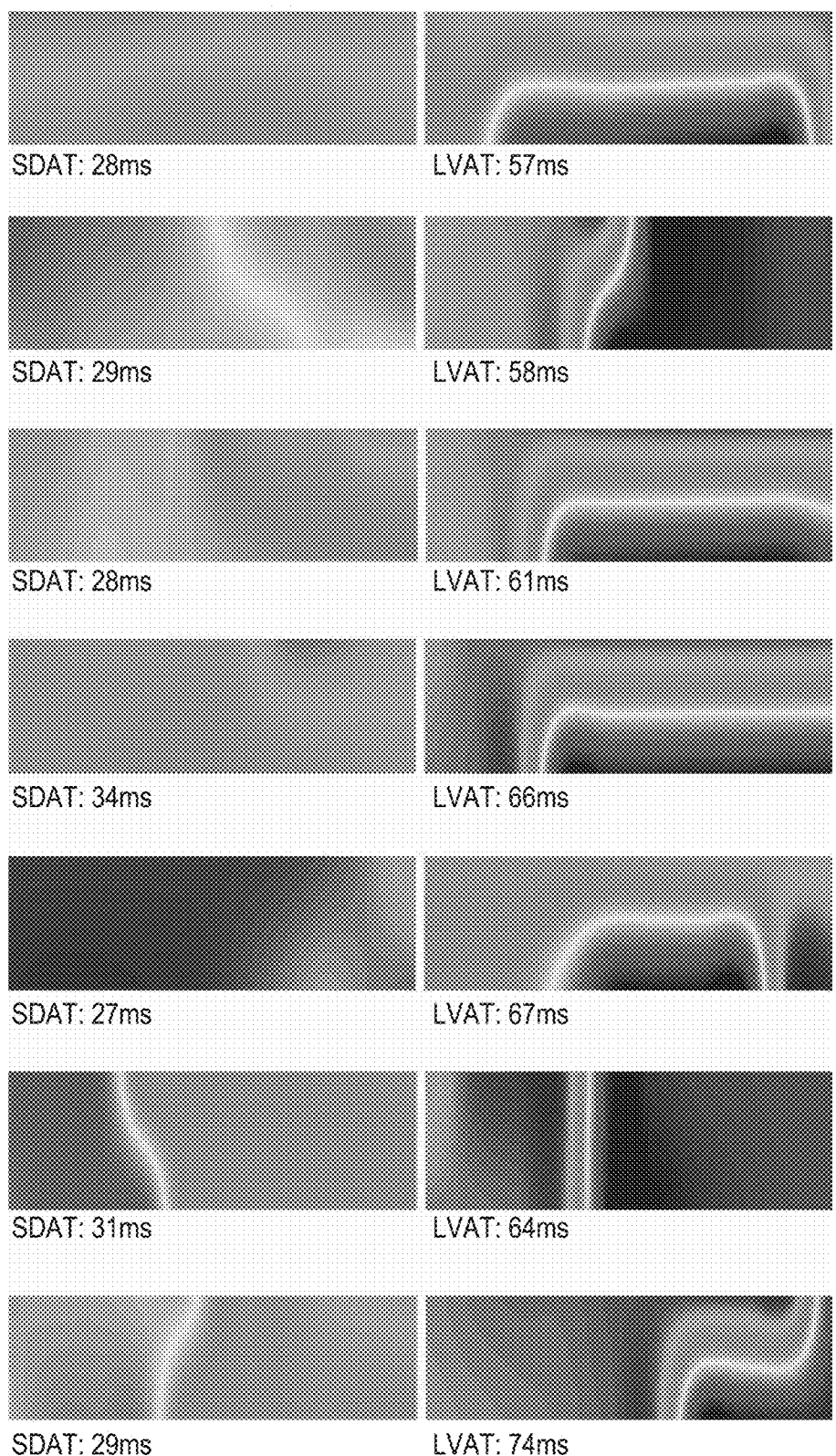
FIG. 5B depicts illustrative anterior and posterior electrical activation maps depicting cardiac resynchronization with partial posterior preactivation during left ventricular basal septal pacing.

Further, for example, seven sets of surrogate electrical activation maps are depicted FIG. 5B that have cardiac resynchronization but with partial posterior preactivation during left ventricular basal septal pacing. Similar to as shown in FIG. 5A, each set includes an anterior activation map on the left, a posterior activation map on the right, and EHI, namely SDAT and LVAT, depicted below each map. As shown, each of the sets has a low SDAT (e.g., less than 35 ms), which may have been provided using a "closed loop" method similar to as described herein with respect to processes 206, 207, 208. However, each of the sets has a relatively-high LVAT (e.g., greater than 50 ms) indicating cardiac resynchronization with partial posterior preactivation.

Figure 5C:
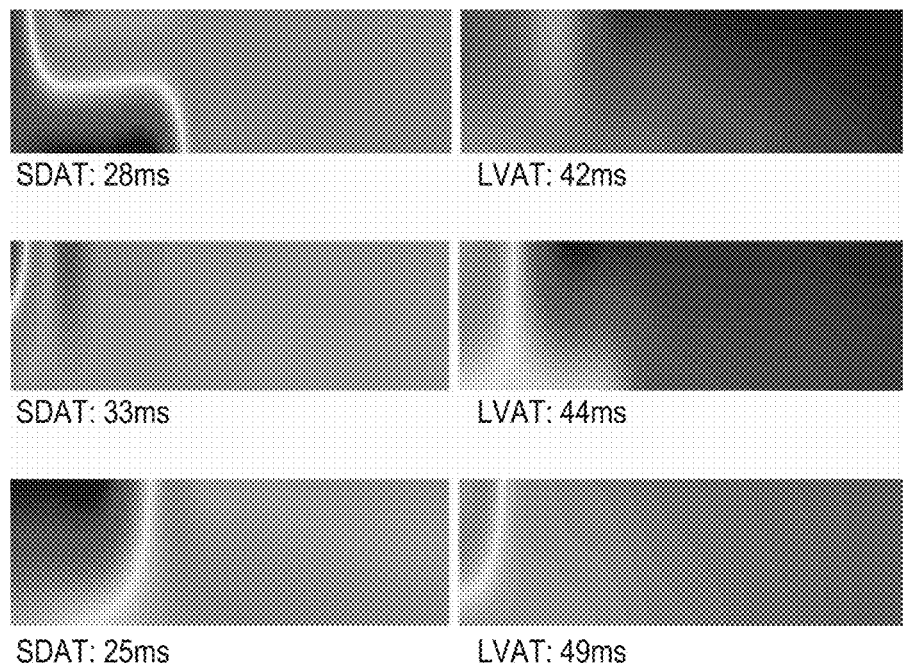
FIG. 5C depicts illustrative anterior and posterior electrical activation maps depicting cardiac resynchronization with complete posterior preactivation with slight left ventricular delay during left ventricular basal septal pacing.

Still further, for example, three sets of surrogate electrical activation maps are depicted in FIG. 5C that have cardiac resynchronization with complete posterior preactivation with slight ventricular delay during left ventricular basal septal pacing. Similar to as shown in FIGS. 5A-5B, each set includes an anterior activation map on the left, a posterior activation map on the right, and EHI, namely SDAT and LVAT, depicted below each map. As shown, each of the sets has a low SDAT (e.g., less than 35 ms), which may have been provided using a "closed loop" method similar to as described herein with respect to processes 206, 207, 208, and a relatively-low LVAT (e.g., less than 50 ms) indicating cardiac resynchronization with complete posterior preactivation with slight left ventricular delay.

Partial posterior preactivation, no posterior preactivation, and complete posterior preactivation with slight left ventricular delay as shown in FIGS. 5A-5C may indicate that a patient may benefit from supplemental cardiac pacing therapy. Thus, supplemental cardiac pacing therapy may be used to supplement the cardiac conduction system pacing therapy when indicated to provide benefit.

The method 200 further includes determining whether supplemental cardiac pacing therapy may be beneficial 210 to be used in conjunction with the cardiac conduction system pacing therapy. The determination of whether supplemental cardiac pacing therapy may be beneficial 210 may be conducted using various metrics and processes.

For example, determination of whether supplemental cardiac pacing therapy may be beneficial 210 may utilize EHI that was generated during processes 206, 207. The EHI may be used to indicate whether the patient's heart has, or is undergoing, left or right ventricular delay despite the delivery of the cardiac conduction system pacing therapy. Left ventricular delay may be a result of left bundle branch block while right ventricular delay may be a result of right bundle branch block. More specifically, such bundle branch blocks may be located "lower" in the cardiac conduction system (e.g., further along the propagation path in the cardiac conduction system) than where the cardiac conduction system pacing therapy is being delivered, and thus, the bundle branch blocks may be "blocking" the pacing pulses from proceeding to one or both ventricles from the cardiac conduction system.

Left ventricular delay may be evaluated using one or more EHI metrics focused on, or directed to, the left ventricular activation. Thus, in one example, LVAT may be used to determine whether supplemental cardiac pacing therapy may be beneficial 210. Various ranges of LVAT may be used to determine the degree of left ventricular delay. For example, complete correction of left heart delay may be indicated by an LVAT that is less than or equal to about 30 ms. Thus, LVAT measured in response to the delivery of cardiac conduction system pacing therapy that is less than or equal to about 30 ms may indicate that supplemental cardiac pacing therapy would not be beneficial to be used in conjunction with the cardiac conduction system pacing therapy.

Further, intermediate correction of left heart delay (e.g., a slight delay in left ventricular activation) may be indicated by an LVAT between about 30 ms and 50 ms such as depicted FIG. 5C, and no or partial correction of left heart delay (e.g., persistent delay in left ventricular activation) may be indicated by an LVAT that is greater than or equal to about 50 ms as shown in FIGS. 5A-5B. Thus, LVAT measured in response to the delivery of cardiac conduction system pacing therapy that is greater about 30 ms and less than 50 ms may indicate that supplemental cardiac pacing therapy may be beneficial to be used in conjunction with the cardiac conduction system pacing therapy, and LVAT measured in response to the delivery of cardiac conduction system pacing therapy that is greater about 50 ms may also indicate that supplemental cardiac pacing therapy may be beneficial to be used in conjunction with the cardiac conduction system pacing therapy.

If it is determined that supplemental cardiac pacing therapy would or may be beneficial, then the method 200 may initiate the delivery of supplemental cardiac pacing therapy to be used in conjunction with the cardiac conduction system pacing therapy 212. As described herein, the supplemental cardiac pacing therapy may delivery pacing therapy to a different area, or portion, of the cardiac conduction system than where cardiac conduction system pacing therapy is already being delivered and/or to areas of the heart other than the cardiac conduction system. For example, supplemental cardiac pacing therapy may include conventional pacing that delivers pacing pulses into myocardial tissue that is not part of the cardiac conduction system of the patient's heart such that, e.g., electrical activation propagates from one myocardial cell to another myocardial cell (also referred to as "cell-to-cell"). For instance, the conventional pacing therapy may deliver pacing pulses directly into the muscular heart tissue that is to be depolarized to provide the contraction of the heart.

The supplemental cardiac pacing therapy may include traditional left ventricular pacing therapy. More specifically, for example, a left ventricular (LV) coronary sinus lead may be implanted so as to extend through one or more veins, the vena cava, the right atrium, and into the coronary sinus to a region adjacent to the free wall of the left ventricle of the heart so as to deliver pacing pulses to the myocardial tissue of the free wall of the left ventricle. Additionally, such supplemental cardiac pacing therapy may be configured (e.g., positioned, implanted, etc.) to provide posterior activation of the left ventricle to provide posterior preactivation resulting in reduced dyssynchrony of the left ventricle.

Further, for example, the supplemental cardiac pacing therapy may include additional cardiac conduction system pacing that delivers pacing pulses into the cardiac conduction system. In other words, the supplemental cardiac pacing therapy may target other parts of the conduction system. For example, a LBB (e.g., VfA lead) may be used as primary cardiac conduction system pacing therapy and the supplemental cardiac pacing therapy may be His bundle or right bundle pacing. Further, for example, in another situation, the primary cardiac conduction system pacing may be His bundle pacing and the supplemental cardiac pacing therapy may be LBB (e.g., VfA) pacing or intraseptal LV pacing.

The supplemental cardiac pacing therapy may be delivered with any type of cardiac pacing systems including a lead, two leads, three leads, and more than three leads. Further, in at least one embodiment, an illustrative device may be implanted in the patient's right atrium and one or more "leadlets," or short leads, may extend from the device to another portion or region of cardiac tissue such as, e.g., another chamber (e.g., left ventricle), a different wall (e.g., free wall of the left ventricle), etc. In one embodiment, a leadlet may extend from a cardiac conduction system pacing device (e.g., implanted in the right atrium) to the left ventricle (e.g., into the coronary sinus to a region adjacent to the free wall of the left ventricle).

Figure 6:
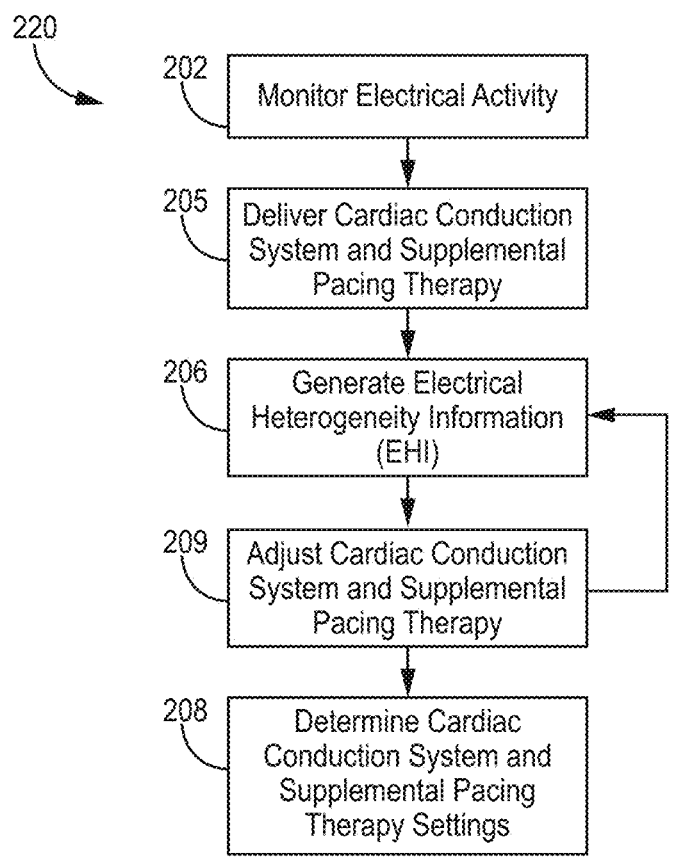
FIG. 6 is a block diagram of an illustrative method of adjusting cardiac conduction system pacing therapy and supplemental cardiac pacing therapy.

Supplemental cardiac pacing therapy used in conjunction with the cardiac conduction system pacing therapy may be adjusted, or modified, (e.g., optimized) to work together in a productive manner to provide effective cardiac therapy and functionality. An illustrative method 220 of adjusting cardiac conduction system pacing therapy and supplemental cardiac pacing therapy is depicted in FIG. 6. The method 220 may include monitoring electrical activity 202 and generating EHI 206, which are similar to the same process 202, 206 described herein with respect to FIG. 4, and as such not further described herein.

The method 220, however, may include delivery of cardiac conduction system pacing therapy and supplemental cardiac pacing therapy 205 and adjusting the cardiac conduction system pacing therapy and supplemental cardiac pacing therapy based on the monitored EHI 209.

For example, EHI may be monitored 209 for an initial configuration of cardiac conduction system pacing therapy and supplemental cardiac pacing therapy, and one or more pacing settings of one or both of the cardiac conduction system pacing therapy and supplemental cardiac pacing therapy may be adjusted, or modified, 209, and then the method 220 may loop back to monitoring EHI 206 and adjusting the one or more pacing settings of one or both of the cardiac conduction system pacing therapy and supplemental cardiac pacing therapy 209. In this way, a plurality of different pacing settings and pacing configurations may be attempted, and EHI for each of the plurality of different pacing settings and pacing configurations may be generated 206.

The plurality of pacing settings of one or both of the cardiac conduction system pacing therapy and supplemental cardiac pacing therapy may include, but not be limited to, supplemental pacing electrode location, supplemental pacing electrode angle, supplemental pacing amplitude or power, supplemental pacing pulse length, supplemental pacing vector, supplemental number of pacing electrodes used, cardiac conduction system pacing electrode location, cardiac conduction system pacing electrode angle, cardiac conduction system pacing amplitude or power, cardiac conduction system pacing pulse length, cardiac conduction system pacing vector, number of cardiac conduction system pacing electrodes used, timing interval between delivery of pacing to the conduction system and delivery of supplemental cardiac pacing, etc. Further, the plurality of pacing settings of one or both of the cardiac conduction system pacing therapy and supplemental cardiac pacing therapy may include various timings such as A-V delay for the supplemental cardiac pacing therapy, V-V delay for the supplemental pacing therapy, A-V delay for the cardiac conduction system pacing therapy, V-V delay for the cardiac conduction system pacing therapy, V-V delay between the cardiac conduction system pacing therapy and the supplemental cardiac pacing therapy. In other words, any one or more pacing settings may be changed (e.g., increase, decreased, moved, etc.) during adjustment of one or both the cardiac conduction system pacing therapy and the supplemental cardiac pacing therapy 209.

As described, EHI for each of the plurality of different pacing settings and pacing configurations may be generated 206, and the method 220 may further include determining selected (e.g., optimal) pacing settings for the cardiac conduction system pacing therapy and the supplemental cardiac pacing therapy 214 based on the generated EHI. In one embodiment, the optimization of a set of parameters related to combined pacing of conduction system and supplemental pacing may be based on achieving complete correction of activation delays in left ventricle. For example, complete correction of activation delays in the left ventricle may be provided when the LVAT is less than 30 ms while maintaining a SDAT less than 25 ms and achieving a reduction of SDAT, relative to the intrinsic SDAT, by greater than or equal to a threshold percentage such as, e.g., 10%, 15%, 20%, 25%, or 30%.

Additionally, it is be understood that although the illustrative systems and methods are directed to supplementing cardiac conduction system pacing therapy, the illustrative systems and methods may be configured to be used to supplement any form or type of cardiac therapy. For example, instead of cardiac conduction system pacing therapy, VfA cardiac pacing therapy may be used to target areas or cells that are not part of the cardiac conduction system or may be used to target endocardial myocytes or areas proximate thereto, and supplemental pacing may be beneficial to be used in conjunction with such VfA cardiac pacing therapy. Thus, the illustrative systems and methods may be used to evaluate if supplemental cardiac pacing therapy could or would benefit such VfA cardiac pacing therapy that is not targeting the cardiac conduction system.

Figure 7:
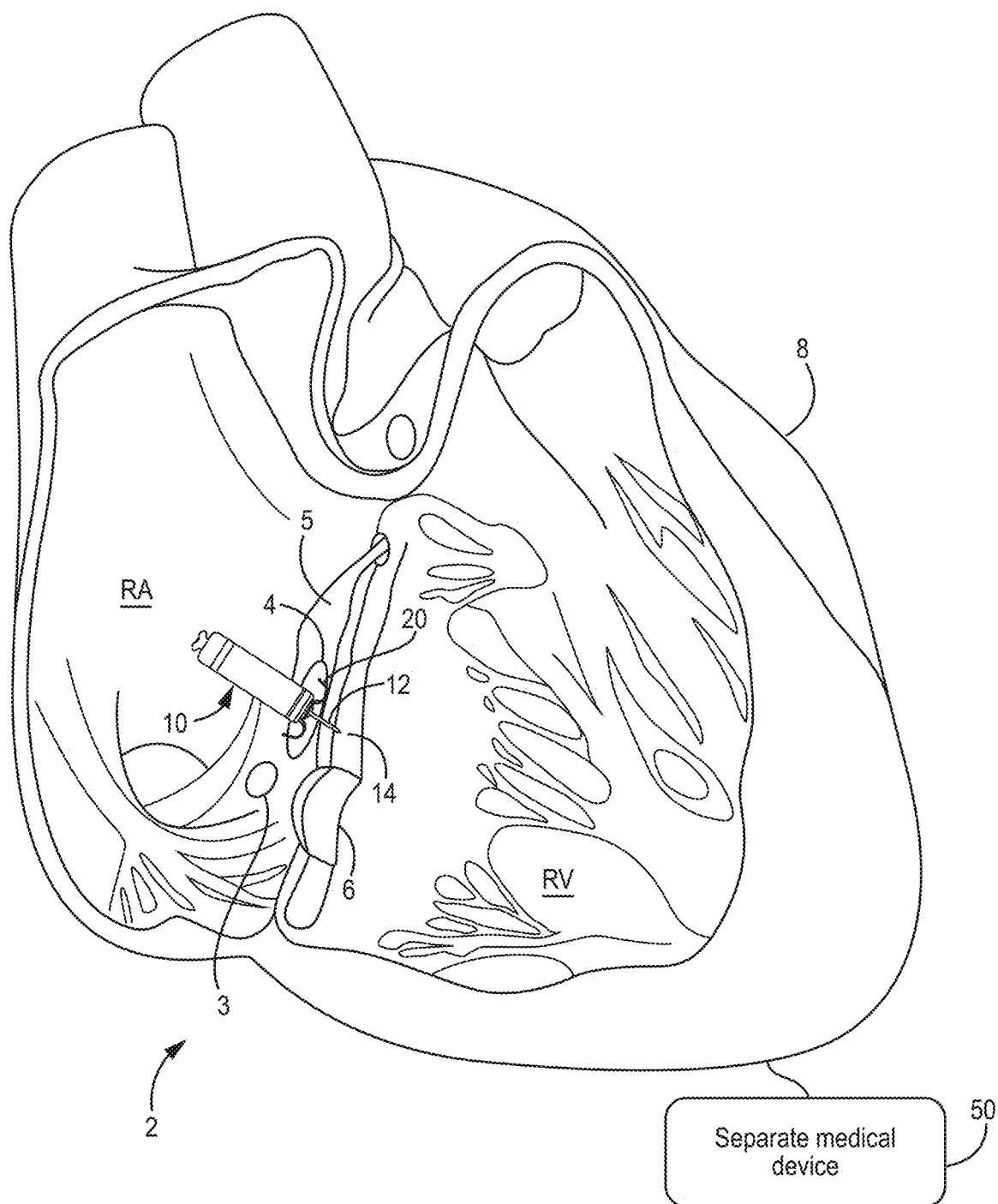
FIG. 7 is a conceptual diagram of an illustrative cardiac therapy system including an intracardiac medical device implanted in a patient's heart and a separate medical device positioned outside of the patient's heart.

An illustrative ventricle from atrium (VfA) cardiac therapy system is depicted in FIG. 7 that may be configured to be used with, for example, the systems and methods described herein with respect to FIGS. 1-6. Although it is to be understood that the present disclosure may utilize one or both of leadless and leaded implantable medical devices, the illustrative cardiac therapy system of FIG. 7 includes a leadless intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device 10 against the atrial endocardium in a target implant region 4. The target implant region 4 may lie between the Bundle of His 5 and the coronary sinus 3 and may be adjacent, or next to, the tricuspid valve 6. The device 10 may be described as a ventricle-from-atrium device because, for example, the device 10 may perform, or execute, one or both of sensing electrical activity from and providing therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. Further, although a leadless device may have a lead, the lead would not extend from outside of the patient's heart to inside of the patient's heart or would not extend from inside of the patient's heart to outside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from a distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at a distal end region of the shaft such that the electrode may be positioned within the ventricular myocardium for sensing ventricular signals and delivering ventricular pacing pulses (e.g., to depolarize the left ventricle and/or right ventricle to initiate a contraction of the left ventricle and/or right ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 7), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 8:
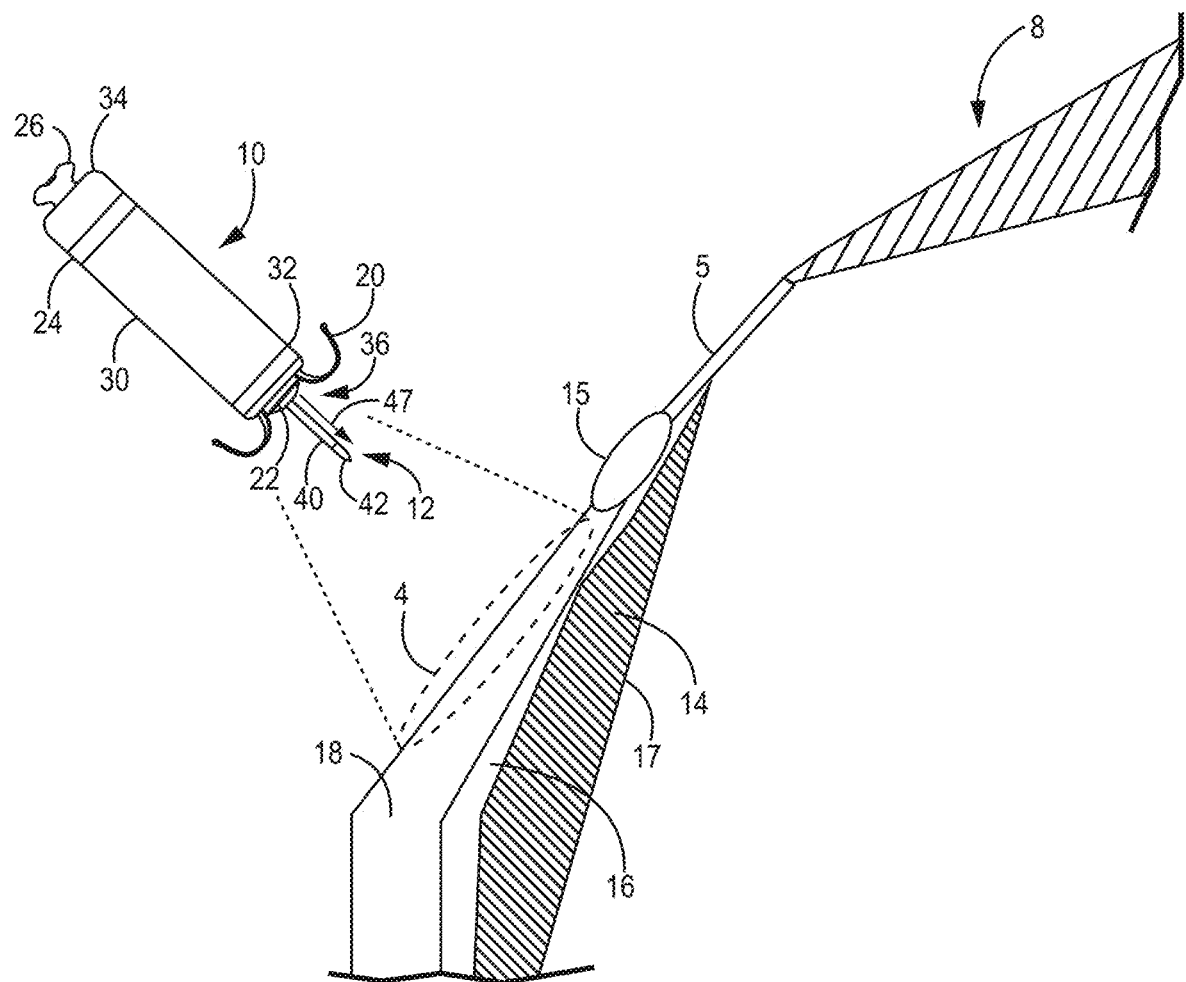
FIG. 8 is an enlarged conceptual diagram of the intracardiac medical device of FIG. 7 and anatomical structures of the patient's heart.

FIG. 8 is an enlarged conceptual diagram of the intracardiac medical device 10 of FIG. 7 and anatomical structures of the patient's heart 8. In particular, the device 10 is configured to sense cardiac signals and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 10. The housing 30 may include (e.g., be formed of or from) an electrically conductive material such as, e.g., titanium or titanium alloy, stainless steel, MP35N (a non-magnetic nickel-cobalt-chromium-molybdenum alloy), platinum alloy, or other bio-compatible metal or metal alloy. In other examples, the housing 30 may include (e.g., be formed of or from) a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 and as defining a generally-cylindrical shape, e.g., to facilitate catheter delivery. In other embodiments, the housing 30 may be prismatic or any other shape to perform the functionality and utility described herein. The housing 30 may include a delivery tool interface member 26, e.g., defined, or positioned, at the proximal end region 34, for engaging with a delivery tool during implantation of the device 10.

All or a portion of the housing 30 may function as a sensing and/or pacing electrode during cardiac therapy. In the example shown, the housing 30 includes a proximal housing-based electrode 24 that circumscribes a proximal portion (e.g., closer to the proximal end region 34 than the distal end region 32) of the housing 30. When the housing 30 is (e.g., defines, formed from, etc.) an electrically-conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to form, or define, the proximal housing-based electrode 24. When the housing 30 is (e.g., defines, formed from, etc.) a non-conductive material, such as a ceramic, glass or polymer material, an electrically-conductive coating or layer, such as a titanium, platinum, stainless steel, or alloys thereof, may be applied to one or more discrete areas of the housing 30 to form, or define, the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32, and therefore, may be referred to as a proximal housing-based electrode 24. In other examples, however, the proximal housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one such example as shown, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemi-spherical distal tip with a relatively narrow tip-diameter (e.g., less than about 1 millimeter (mm)) for penetrating into and through tissue layers without using a sharpened tip or needle-like tip having sharpened or beveled edges.

The dart electrode assembly 12 may be configured to pierce through one or more tissue layers to position the tip electrode 42 within a desired tissue layer such as, e.g., the ventricular myocardium. As such, the height 47, or length, of the shaft 40 may correspond to the expected pacing site depth, and the shaft 40 may have a relatively-high compressive strength along its longitudinal axis to resist bending in a lateral or radial direction when pressed against and into the implant region 4. If a second dart electrode assembly 12 is employed, its length may be unequal to the expected pacing site depth and may be configured to act as an indifferent electrode for delivering of pacing energy to and/or sensing signals from the tissue. In one embodiment, a longitudinal axial force may be applied against the tip electrode 42, e.g., by applying longitudinal pushing force to the proximal end 34 of the housing 30, to advance the dart electrode assembly 12 into the tissue within the target implant region.

The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. Thus, the dart electrode assembly 12 including the shaft 40 may be described as being resilient. When the shaft 40 is not exposed to any external force, or to only a force along its longitudinal central axis, the shaft 40 may retain a straight, linear position as shown.

In other words, the shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by a height, or length, 47 of the shaft 40.

The one or more fixation members 20 may be described as one or more "tines" having a normally curved position. The tines may be held in a distally extended position within a delivery tool. The distal tips of tines may penetrate the heart tissue to a limited depth before elastically, or resiliently, curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of tip electrode 42 and shaft 40 from about 3 mm to about 8 mm in various examples. The diameter of the shaft 40 may be less than about 2 mm, and may be about 1 mm or less, or even about 0.6 mm or less.

Figure 9:
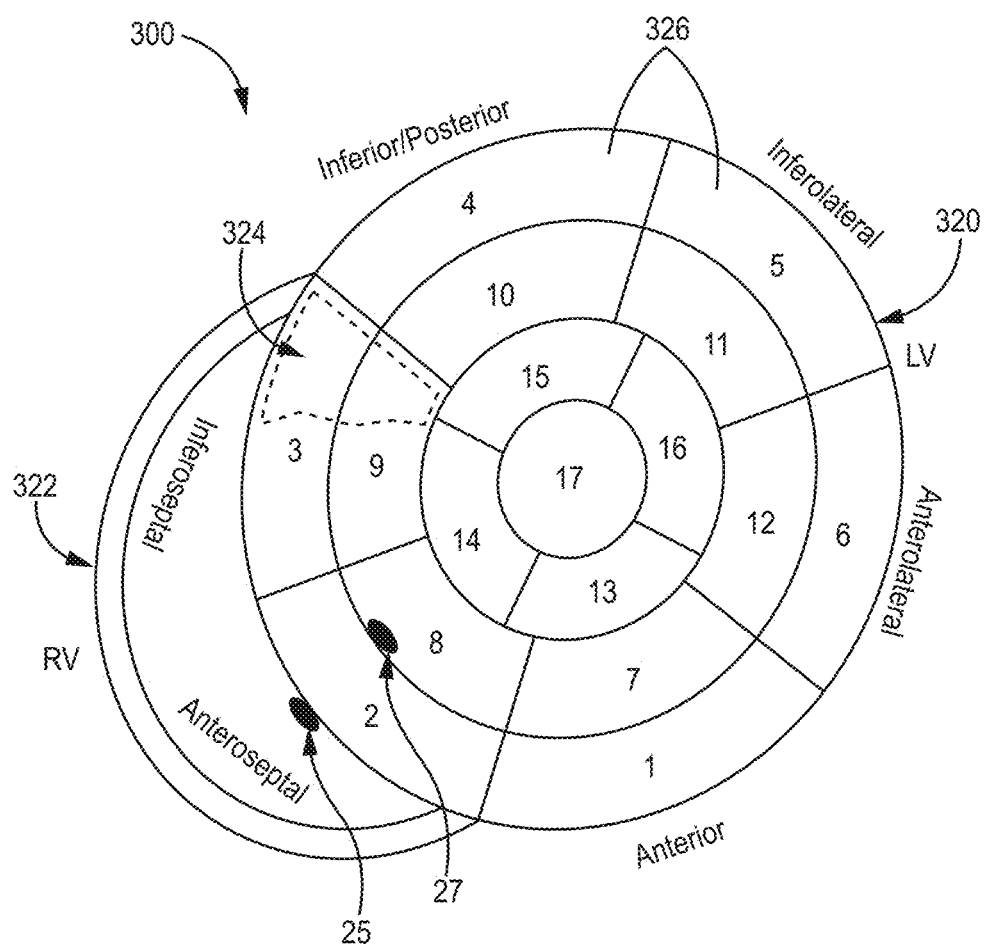
FIG. 9 is a conceptual diagram of a map of a patient's heart in a standard 17 segment view of the left ventricle showing various electrode implantation locations for use with the illustrative systems and devices described herein.

FIG. 9 is a two-dimensional (2D) ventricular map 300 of a patient's heart (e.g., a top-down view) showing the left ventricle 320 in a standard 17 segment view and the right ventricle 322. The map 300 defines, or includes, a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) 25 and left bundle branch (LBB) 27.

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body. Once implanted, the tissue-piercing electrode may be positioned in the target implant region 4 (FIGS. 7-8), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 10:
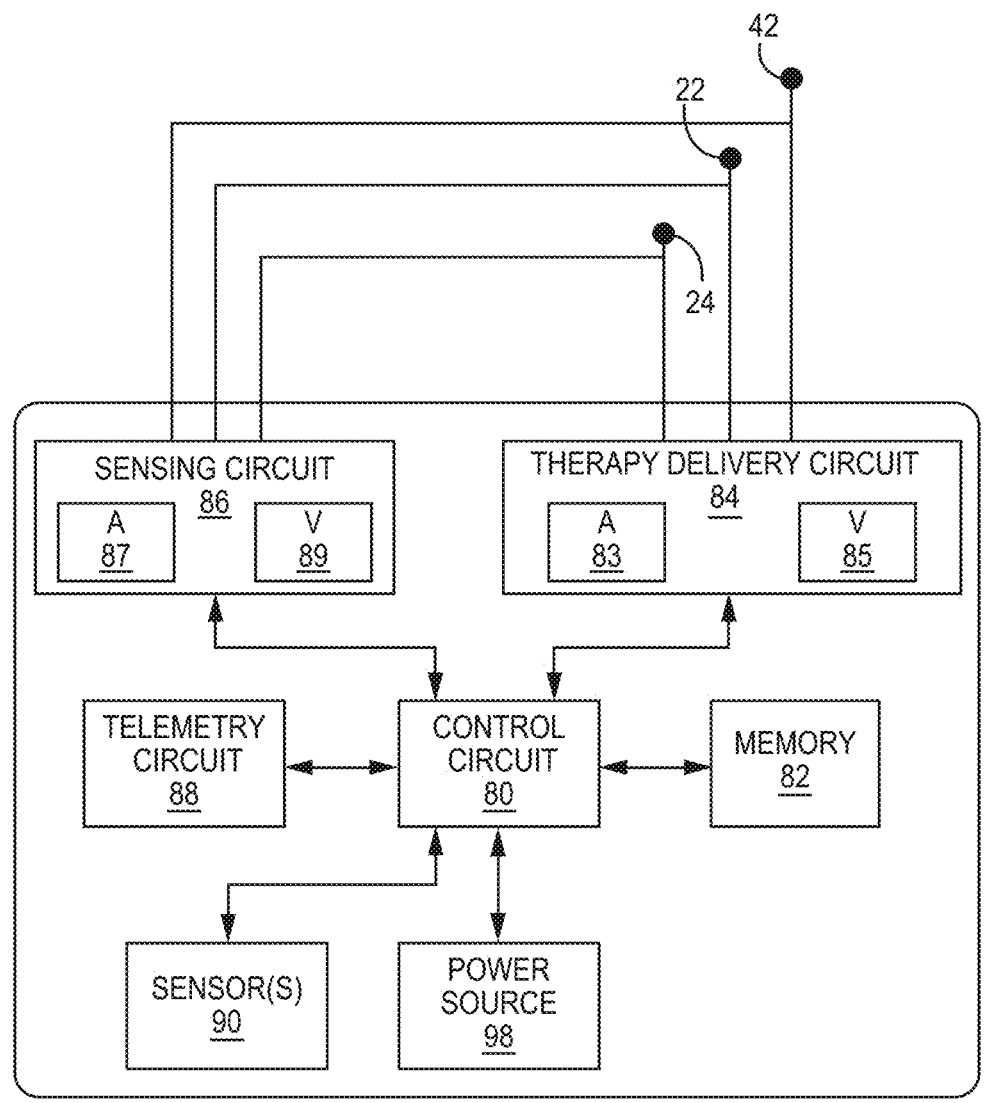
FIG. 10 is a block diagram of illustrative circuitry that may be enclosed within the housing of the medical devices of FIGS. 7-8, for example, to provide the functionality and therapy described herein.

A block diagram of circuitry is depicted in FIG. 10 that may be enclosed within the housings 30 of the device 10 to provide the functions of sensing cardiac signals, determining capture, and/or delivering pacing therapy according to one example or within the housings of any other medical devices described herein. The separate medical device 50 as shown in FIG. 7 may include some or all the same components, which may be configured in a similar manner. The electronic circuitry enclosed within the housing 30 may include software, firmware, and hardware that cooperatively monitor atrial and ventricular electrical cardiac signals, determine whether cardiac system capture has occurred, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing signals that are correlated to one or more physiological functions, states, or conditions of the patient. For example, the sensor(s) 90 may include a patient activity sensor, for use in determining a need for pacing therapy and/or controlling a pacing rate. In other words, the device 10 may include other sensors 90 for sensing signals from the patient for use in determining whether to deliver and/or controlling electrical stimulation therapies delivered by the therapy delivery circuit 84.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90 may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown in FIG. 10 represent functionality included in the device 10 and may include any discrete and/or integrated electronic circuit components that implement analog, and/or digital circuits capable of producing the functions attributed to the medical device 10 described herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to determine cardiac conduction system capture and/or perform a single, dual, or triple chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analogto-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (A-V) pacing interval. If an R-wave is sensed before the A-V pacing interval expires, the ventricular pacing pulse may be inhibited. If the A-V pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an A-V or V-V pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an A-V pacing interval in response to a delivered atrial pacing pulse to provide synchronized multiple chamber pacing (e.g., dual or triple chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

The techniques described in this disclosure, including those attributed to the IMD 10, device 50, the computing apparatus 140, and the computing device 160 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all the listed elements or a combination of at least two of the listed elements. The phrases "at least one of," "comprises at least one of," and "one or more of" followed by a list refers to any one of the items in the list and any combination of two or more items in the list.

Illustrative Embodiments

Embodiment 1: A system comprising:
electrode apparatus comprising a plurality of electrodes to monitor electrical activity from tissue of a patient; and
computing apparatus comprising processing circuitry and coupled to the electrode apparatus and configured to:
  monitor electrical activity of the patient's heart using one or more electrodes of the plurality of electrodes during delivery of cardiac conduction system pacing therapy,
  generate electrical heterogeneity information (EHI) based on the monitored electrical activity during delivery of cardiac conduction system pacing therapy, and
  determine whether the cardiac conduction system pacing therapy would benefit from supplemental cardiac pacing therapy based on the generated EHI.

Embodiment 2: A method comprising:
monitoring electrical activity of the patient's heart using one or more electrodes of a plurality of electrodes during delivery of cardiac conduction system pacing therapy;
generating electrical heterogeneity information (EHI) based on the monitored electrical activity during delivery of cardiac conduction system pacing therapy; and
determining whether the cardiac conduction system pacing therapy would benefit from supplemental cardiac pacing therapy based on the generated EHI.

Embodiment 3: The system or method as set forth in one of embodiments 1-2, wherein the cardiac conduction system pacing therapy is ventricle-from-atrium (VfA) pacing therapy.

Embodiment 4: The system or method as set forth in one of embodiments 1-2, wherein the cardiac conduction system pacing therapy comprises one or more of His bundle pacing therapy and intraseptal left ventricular endocardial pacing.

Embodiment 5: The system or method as set forth in one of embodiments 1-4, wherein determining whether the cardiac conduction system pacing therapy would benefit from supplemental cardiac pacing therapy based on the generated EHI comprises determining whether the patient's heart has left ventricular delay or determining a degree of correction of left ventricular delay of the patient's heart by the cardiac conduction system pacing.

Embodiment 6: The system or method as set forth in one of embodiments 1-5, wherein the supplemental cardiac pacing therapy comprises left ventricular pacing therapy.

Embodiment 7: The system or method as set forth in one of embodiments 1-6, wherein the plurality of electrodes comprises two or more left electrodes to be located proximate the left side of the patient, wherein generating electrical heterogeneity information (EHI) based on the monitored electrical activity during delivery of cardiac conduction system pacing therapy comprises generating a left metric of surrogate electrical activation times monitored by the two or more left electrodes during delivery of cardiac conduction system pacing.

Embodiment 8: The system or method as set forth in embodiment 7, wherein the left metric of surrogate electrical activation times comprises a left average of surrogate electrical activation times monitored by the two or more left electrodes.

Embodiment 9: The system or method as set forth in one of embodiments 1-8, wherein the computing apparatus is further configured to execute or the method further comprises adjusting the cardiac conduction system pacing therapy prior to determining whether the cardiac conduction system pacing therapy would benefit from supplemental cardiac pacing therapy.

Embodiment 10: The system or method as set forth in one of embodiments 1-9, wherein the plurality of electrodes comprises a plurality of external surface electrodes positioned in an array to be located proximate skin of a torso of the patient.

Embodiment 11: A system comprising:
electrode apparatus comprising a plurality of electrodes to monitor electrical activity from tissue of a patient; and
computing apparatus comprising processing circuitry and coupled to the electrode apparatus and configured to:
monitor electrical activity of the patient's heart using one or more electrodes of the plurality of electrodes during delivery of cardiac conduction system pacing therapy and supplemental cardiac pacing therapy,
generate electrical heterogeneity information (EHI) based on the monitored electrical activity during delivery of cardiac conduction system pacing therapy and supplemental cardiac pacing therapy, and
adjust one or more pacing settings of one or both of cardiac conduction system pacing therapy and supplemental cardiac pacing therapy based on the generated EHI.

Embodiment 12: The system as set forth in embodiment 11, wherein the cardiac conduction system pacing therapy comprises one or more of ventricle-from-atrium (VfA) pacing therapy, His bundle pacing therapy, and intraseptal left ventricular endocardial pacing.

Embodiment 13: The system as set forth in one of embodiments 11-12, wherein the supplemental cardiac pacing therapy comprises left ventricular pacing therapy.

Embodiment 14: The system as set forth in one of embodiments 11-13, wherein the plurality of electrodes comprises two or more left external electrodes to be located proximate the left side of the patient, wherein generating electrical heterogeneity information (EHI) based on the monitored electrical activity during delivery of cardiac conduction system pacing therapy comprises generating a left metric of surrogate electrical activation times monitored by the two or more left external electrodes during delivery of cardiac conduction system pacing.

Embodiment 15: The system as set forth in embodiment 14, wherein the left metric of surrogate electrical activation times comprises a left average of surrogate electrical activation times monitored by the two or more left external electrodes.

Embodiment 16: The system as set forth in one of embodiments 11-15, wherein the one or more pacing settings comprises a V-V delay between a pacing pulse of the cardiac conduction system pacing therapy and a ventricular pacing pulse of the supplemental cardiac pacing therapy.

Embodiment 17: The system as set forth in one of embodiments 11-16, wherein the one or more pacing settings comprises one or more of cardiac conduction system pacing electrode position, cardiac pacing electrode position, pacing vector, amplitude, and A-V delay.

Embodiment 18: The system as set forth in one of embodiments 11-17, wherein the plurality of electrodes comprises a plurality of external surface electrodes positioned in an array to be located proximate skin of a torso of the patient.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A system comprising:
an implantable medical device comprising a first implantable electrode, a second implantable electrode, and a first computing apparatus comprising processing circuitry and configured to deliver a cardiac conduction system pacing therapy using the first implantable electrode; and
an evaluation apparatus comprising:
an electrode apparatus comprising a plurality of electrodes to monitor electrical activity from tissue of a patient; and
a second computing apparatus comprising processing circuitry and coupled to the electrode apparatus and configured to:
monitor electrical activity of the patient's heart using the plurality of electrodes during the delivery of the cardiac conduction system pacing therapy using the implantable medical device,
determine activation times during the delivery of the cardiac conduction system pacing therapy based on the monitored electrical activity,
generate electrical heterogeneity information (EHI) based on the determined activation times, and
determine whether the cardiac conduction system pacing therapy would benefit from a supplemental cardiac pacing therapy based on the generated EHI,
wherein the first computing apparatus is further configured to:
deliver the supplemental cardiac pacing therapy using the second implantable electrode in response to determining that the cardiac conduction system pacing therapy would benefit from the supplemental cardiac pacing therapy, and
continue the delivery of the cardiac conduction system pacing therapy using the first implantable electrode in response to determining that the cardiac conduction system pacing therapy would not benefit from the supplemental cardiac pacing therapy.

2. The system of claim 1, wherein the cardiac conduction system pacing therapy is ventricle-from-atrium (VfA) pacing therapy.

3. The system of claim 1, wherein the cardiac conduction system pacing therapy comprises one or more of His bundle pacing therapy and intraseptal left ventricular endocardial pacing.

4. The system of claim 1, wherein determining whether the cardiac conduction system pacing therapy would benefit from supplemental cardiac pacing therapy based on the determined activation times comprises determining a degree of correction of left ventricular delay of the patient's heart by the cardiac conduction system pacing.

5. The system of claim 1, wherein the supplemental cardiac pacing therapy comprises left ventricular pacing therapy.

6. The system of claim 1, wherein the plurality of electrodes comprises two or more left electrodes to be located proximate the left side of the patient, wherein determining activation times during the delivery of the cardiac conduction system pacing therapy based on the monitored electrical activity comprises generating a left metric of surrogate electrical activation times monitored by the two or more left electrodes during delivery of cardiac conduction system pacing.

7. The system of claim 6, wherein the left metric of surrogate electrical activation times comprises a left average of surrogate electrical activation times monitored by the two or more left electrodes.

8. The system of claim 1, wherein the first computing apparatus is further configured to optimize the cardiac conduction system pacing therapy prior to the second computing apparatus determining whether the cardiac conduction system pacing therapy would benefit from supplemental cardiac pacing therapy.

9. The system of claim 1, wherein the plurality of electrodes comprises a plurality of external surface electrodes positioned in an array to be located proximate skin of a torso of the patient.

10. A method comprising:
  initiating delivery of a cardiac conduction system pacing therapy,
  monitoring electrical activity of the patient's heart using a plurality of electrodes during the delivery of the cardiac conduction system pacing therapy;
  determining activation times during the delivery of the cardiac conduction system pacing therapy based on the monitored electrical activity;
  generating electrical heterogeneity information (EHI) based on the determined activation times;
  determining whether the cardiac conduction system pacing therapy would benefit from supplemental cardiac pacing therapy based on the generated EHI;
  initiating delivery of the supplemental cardiac pacing therapy in response to determining that the cardiac conduction system pacing therapy would benefit from the supplemental cardiac pacing therapy; and
  continuing the delivery of the cardiac conduction system pacing therapy in response to determining that the cardiac conduction system pacing therapy would not benefit from the supplemental cardiac pacing therapy.

11. The method of claim 10, wherein the cardiac conduction system pacing therapy is ventricle-from-atrium (VfA) pacing therapy.

12. The method of claim 10, wherein the cardiac conduction system pacing therapy comprises one or more of His bundle pacing therapy and intraseptal left ventricular endocardial pacing.

13. The method of claim 10, wherein determining whether the cardiac conduction system pacing therapy would benefit from supplemental cardiac pacing therapy based on the determined activation times comprises determining a degree of correction of left ventricular delay of the patient's heart by the cardiac conduction system pacing.

14. The method of claim 10, wherein the supplemental cardiac pacing therapy comprises left ventricular pacing therapy.

15. The method of claim 10, wherein the plurality of electrodes comprises two or more left electrodes to be located proximate the left side of the patient, wherein determining activation times during the delivery of the cardiac conduction system pacing therapy based on the monitored electrical activity comprises generating a left metric of surrogate electrical activation times monitored by the two or more left electrodes during delivery of cardiac conduction system pacing.

16. The method of claim 15, wherein the left metric of surrogate electrical activation times comprises a left average of surrogate electrical activation times monitored by the two or more left electrodes.

17. The method of claim 10, wherein the method further comprises optimizing the cardiac conduction system pacing therapy prior to determining whether the cardiac conduction system pacing therapy would benefit from supplemental cardiac pacing therapy.

18. The method of claim 10, wherein the plurality of electrodes comprises a plurality of external surface electrodes positioned in an array located proximate skin of a torso of the patient.

19. A system comprising:
  an implantable medical device comprising a first implantable electrode, a second implantable electrode, and a first computing apparatus comprising processing circuitry and configured to:
    deliver a cardiac conduction system pacing therapy using the first implantable electrode and deliver a supplemental cardiac pacing therapy using the second implantable electrode; and
  an evaluation apparatus comprising:
    an electrode apparatus comprising a plurality of electrodes to monitor electrical activity from tissue of a patient; and
    a second computing apparatus comprising processing circuitry and coupled to the electrode apparatus and configured to:
      monitor electrical activity of the patient's heart using the plurality of electrodes during the delivery of the cardiac conduction system pacing therapy and the supplemental cardiac pacing therapy using the implantable medical device,
      determine activation times during the delivery of the cardiac conduction system pacing therapy and the supplemental cardiac pacing therapy based on the monitored electrical activity,
      generate electrical heterogeneity information (EHI) based on the determined activation times, and
      determine whether at least one of the cardiac conduction system pacing therapy and the supplemental cardiac pacing therapy would benefit from one or more adjustments to pacing settings of the cardiac conduction system pacing therapy and the supplemental cardiac pacing therapy based on the generated EHI, wherein the first computing apparatus is further configured to:
adjust one or more pacing settings of one or both of cardiac conduction system pacing therapy delivered using the first implantable electrode and supplemental cardiac pacing therapy delivered using the second implantable electrode in response to determining that at least one of the cardiac conduction system pacing therapy and the supplemental cardiac pacing therapy would benefit from one or more adjustments to pacing settings, and continue the delivery of the cardiac conduction system pacing therapy using the first implantable electrode and continue the delivery of the supplemental cardiac pacing therapy using the second implantable electrode in response to determining that the cardiac conduction system pacing therapy and the supplemental cardiac pacing therapy would not benefit from one or more adjustments to pacing settings.

20. The system of claim 19, wherein the cardiac conduction system pacing therapy comprises one or more of ventricle-from-atrium (VfA) pacing therapy, His bundle pacing therapy, and intraseptal left ventricular endocardial pacing.

21. The system of claim 19, wherein the supplemental cardiac pacing therapy comprises left ventricular pacing therapy.

22. The system of claim 19, wherein the plurality of electrodes comprises two or more left external electrodes to be located proximate the left side of the patient, wherein determining activation times during the delivery of the cardiac conduction system pacing therapy and the supplemental cardiac pacing therapy based on the monitored electrical activity comprises generating a left metric of surrogate electrical activation times monitored by the two or more left external electrodes during delivery of cardiac conduction system pacing.

23. The system of claim 22, wherein the left metric of surrogate electrical activation times comprises a left average of surrogate electrical activation times monitored by the two or more left external electrodes.

24. The system of claim 19, wherein the one or more pacing settings comprises a V-V delay between a pacing pulse of the cardiac conduction system pacing therapy and a ventricular pacing pulse of the supplemental cardiac pacing therapy.

25. The system of claim 19, wherein the one or more pacing settings comprises one or more of cardiac conduction system pacing electrode position, cardiac pacing electrode position, pacing vector, amplitude, and A-V delay.

26. The system of claim 19, wherein the plurality of electrodes comprises a plurality of external surface electrodes positioned in an array to be located proximate skin of a torso of the patient.

* * * * *